United States Patent [19]

Jessen

[11] 4,291,690
[45] Sep. 29, 1981

[54] MEANS FOR PERFORMING AN EMERGENCY CRICOTHYROTOMY

[76] Inventor: John W. Jessen, 421 Keeney, Evanston, Ill. 60202

[21] Appl. No.: 22,424

[22] Filed: Mar. 21, 1979

[51] Int. Cl.³ .................. A61B 17/32; A61M 16/00
[52] U.S. Cl. ......................... 128/200.26; 128/305.3
[58] Field of Search .................. 128/347, 351, 200.26, 128/345, 305.3, 348, 207.14, 329 R, DIG. 26

[56] References Cited

U.S. PATENT DOCUMENTS 3,713,447  1/1973  Adair .................................. 128/347
3,916,903  11/1975  Pozzi .................................. 128/305.3

FOREIGN PATENT DOCUMENTS 291712  6/1971  U.S.S.R. ......................... 128/200.26

*Primary Examiner*—Robert W. Michell
*Assistant Examiner*—Michael H. Thaler
*Attorney, Agent, or Firm*—Laff, Whitesel & Rockman

[57] ABSTRACT

A self-contained, presterilized trocar assembly, with an outer cannula and cutting stylet, is just long enough to penetrate the skin of the throat and the cricothyroid membrane and reach the posterior third of the lumen of an average adult trachea. Its short length and self-limiting penetration preclude damage to surrounding tissues. The cannula retains its intratracheal position by a flaring of its distal end after insertion and during a final stage in the deployment. This device enables an unassisted person operating in extreme emergency conditions to establish, quickly and safely, an emergency percutaneous transtracheal airway for a choking person. The tissue damage resulting from the application of the device is minimal, and the incision can be closed with surgical tape.

9 Claims, 12 Drawing Figures

MEANS FOR PERFORMING AN EMERGENCY CRICOTHYROTOMY

This invention relates to emergency cricothyrotomy devices and, more particularly, to trocars for enabling medical and paramedical personnel to safely perform emergency airway operations by means of a cricothyrotomy.

A cricothyrotomy is an emergency procedure performed on a choking person to admit air into the lungs via an opening made in the cricothyroid membrane. The cricothyroid membrane lies between the cricoid and thyroid cartilages of the voice box and is easily located by palpation of the larynx and trachea. Only the thin skin of the throat covers the membrane; no large blood vessels, glands, or other critical structures are normally encountered if this site is used. Though this area is not well-suited to long-term, auxillary airway maintenance, it offers the safest and most direct access in times of emergency. Presently available devices and methods for performing an emergency cricothyrotomy, however, have serious drawbacks for inexperienced personnel and are of limited effectiveness.

A tracheotomy is a surgical procedure used to admit air into the lungs when the normal breathing passage is obstructed or otherwise ceases to function properly. Briefly stated, a tracheotomy usually involves an incision through the skin of the neck below the level of the voice box and careful manipulation of the thyroid gland and several large blood vessels to expose the trachea. A small circular opening is made in the trachea and an endotracheal tube is inserted to maintain the opening and provide an airway. A tracheotomy is the procedure of choice when an auxillary airway is to be maintained for an extended period. It is a delicate operation requiring the skill and knowledge of a surgeon and the facilities of a hospital emergency room. Unfortunately, the services of a surgeon and hospital facilities are usually not immediately available to someone who is choking. Unless the patient is given means to breathe, he will die in approximately three minutes. There are well-established non-surgical techniques for removing a supralaryngeal airway obstruction which should be utilized, whenever possible, before any surgical technique is applied. However, these non-surgical methods have a limited range of applicability and are sometimes ineffective. Therefore, there is a need for a device which will enable a person with limited training to provide an emergency airway at any location where a choking emergency occurs.

Accordingly, an object of the invention is to provide a device for performing an emergency percutaneous transtracheal airway procedure for an individual who develops an acute supralaryngeal airway obstruction. Here, an object is to provide an airway which is large enough to enable the patient to breathe without the aid of high-pressure gas exchange equipment and to facilitate ventilation of a patient, who is not breathing, by a mouth-to-cannula resuscitation technique.

Another object of the invention is to provide a funnel-shaped receiver, on a cannula unit, which is compatible with standard resuscitation equipment. Here, an object is to also provide a cannula with a bore diameter (approximately 6 mm) large enough to enable passage of a suction catheter for aspiration of intratracheal fluid.

Still another object of the invention is to provide a small, durable, self-contained, pre-sterilized unit which can be conveniently carried and almost instantly applied. The capsular package design and the simple straight-in, straight-out deployment procedure allows the unit to be opened and applied during a period which might be on the order of 15 seconds or less.

In keeping with the various aspects of the invention, these and other objects are accomplished by a trocar having a lancet cutting end designed to enable it to penetrate only the thin, tightly drawn tissue over the cricothyroid membrane. Because the device is placed straight into the trachea, the only structure which the cutting edge may contact if the unit is pushed with excessive force into the throat upon insertion is the thick posterior wall of the cricoid cartilage which the lancet cannot penetrate. This guards against perforation of the esophagus. The trocar is very short, only long enough to come to rest within the posterior third of the lumen of an average adult trachea, which generally precludes possible damage to nearby structures. Other presently available devices have longer, curved trocars which require complex insertion techniques and have the potential to severely damage surrounding tissues.

As a result of an intratracheal retention of the cannula unit provided by the flaring of its distal end during deployment, no additional means of fixation are necessary to maintain the airway. The tissue damage resulting from the application of the device is minimal. After removal of the cannula, the tiny incision made by the lancet can be closed with surgical tape. This device, then, enables unassisted individuals with minimal training, under life-threatening emergency conditions, to quickly establish a percutaneous transtracheal airway which is compatible with conventional resuscitation and suction equipment.

The invention may be understood from a study of the attached drawings wherein.

Figure 8:
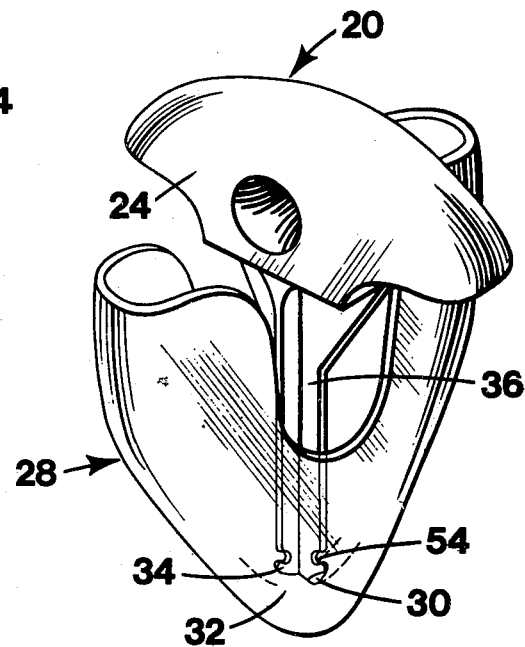
Figure 9:
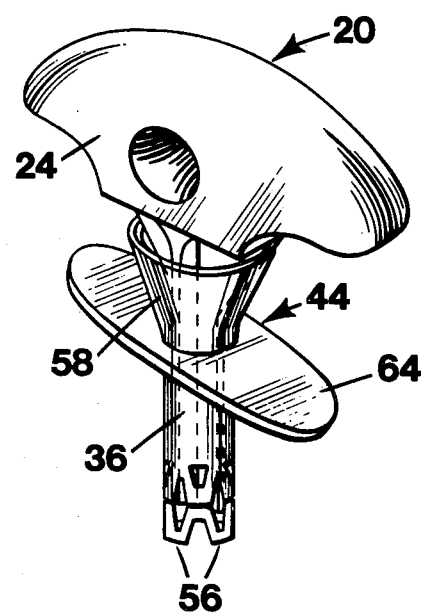
Figure 10:
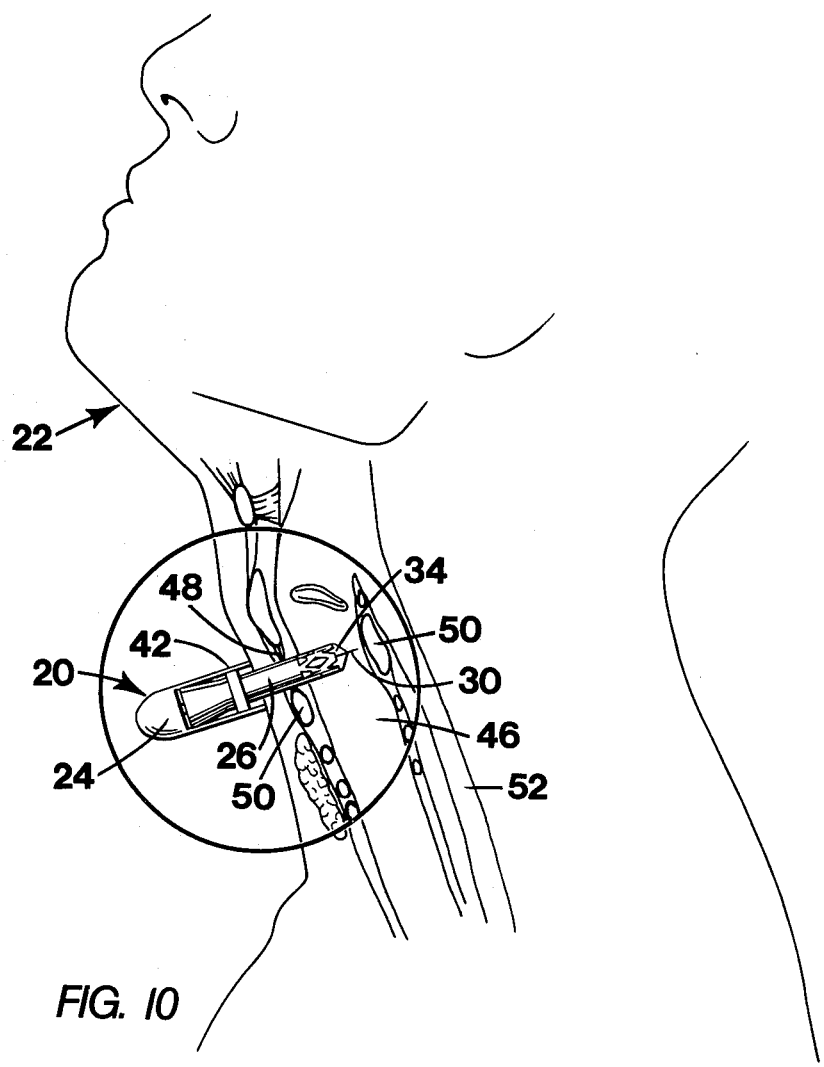
Figure 11:
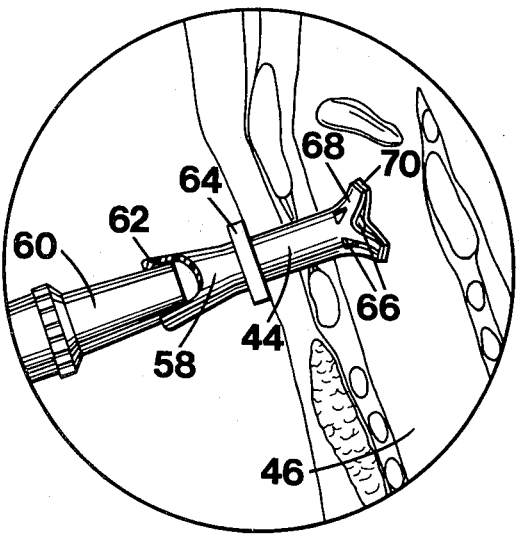
Figure 12:
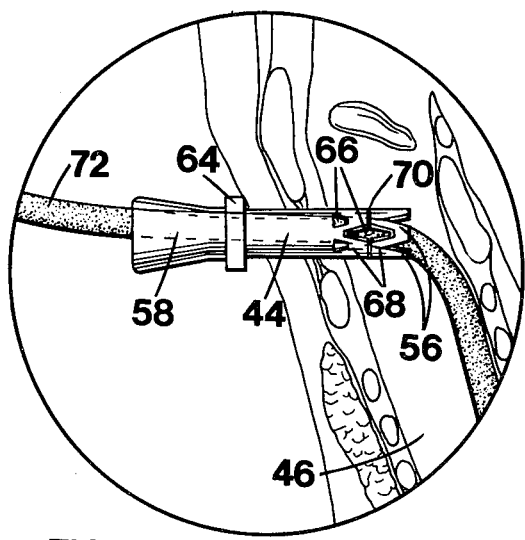

FIG. 8 schematically shows how the handle-stylet and scabbard blade-guard are reassembled for a blunting of the stylet to remove the cannula;

FIG. 9 schematically shows the blunted stylet within the cannula and the resultant eversion of the flared distal end necessary for withdrawal;

FIG. 10 schematically shows the position of the inventive trocar within the trachea after insertion;

FIG. 11 schematically shows that portion of FIG. 10 which is encircled, wherein the fully deployed cannula unit of the inventive trocar is within the trachea and an endotracheal tube adaptor is affixed within its funnel-shaped receiver; and FIG. 12 schematically shows that portion of FIG. 10 which is encircled, wherein the cannula unit is positioned within the trachea and a suction catheter passes through it for aspiration of intratracheal fluid.

Figure 1:
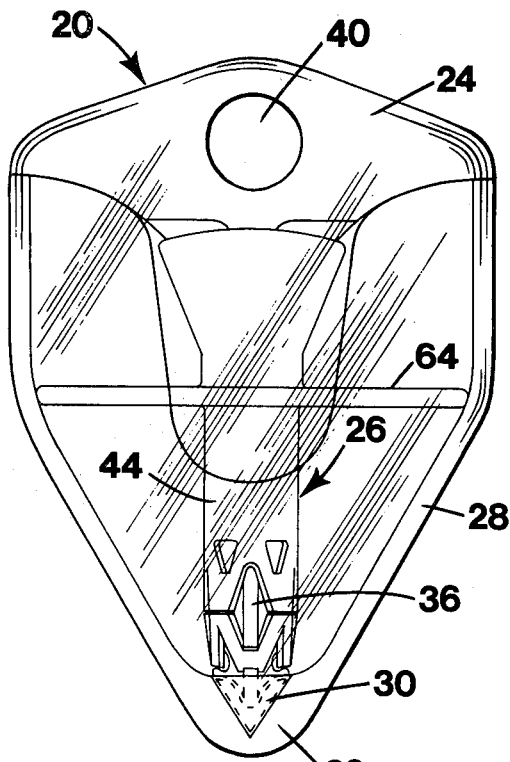
FIG. 1 is a front elevation view of the inventive device as it appears prior to opening and deployment.
Figure 2:
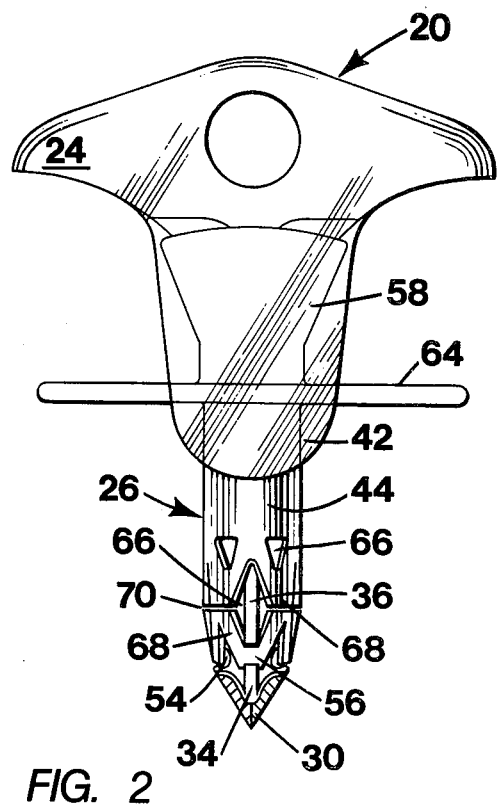
FIG. 2 is a similar elevation view of the device with the bottom half of its case removed, ready for application to a patient.

The inventive, cricothyrotomy device 20 (FIGS. 1, 2) provides for percutaneous transtracheal ventilation of a patient 22 (FIG. 10) with an acute supralaryngeal airway obstruction. The injection-molded clear plastic case is composed of an upper half, comprising the handle 24 and trocar assembly 26, and a lower half 28 which serves as a scabbard. These two upper and lower parts fit together to form a durable capsule which protects the unit and keeps it sterile (FIGS. 1, 2). Sterility is further guaranteed and preserved by covering the exterior of the case with a clear plastic coating (not shown) which has a seam pressed in along the junction of the two halves. The halves of the case are preferably welded together at several points (not shown). Therefore, a squeezing of the sides of the case fractures the welds and allows the separation of the handle 24 from the scabbard 28. Pulling them apart tears the outer coating along its seam, thus exposing a sharpened surgical steel lancet tip 30 (noted by cross-hatching in FIGS. 2, 3 and 7) on the distal end of the trocar assembly 26 and readying the unit for application (FIG. 2).

Figure 7:
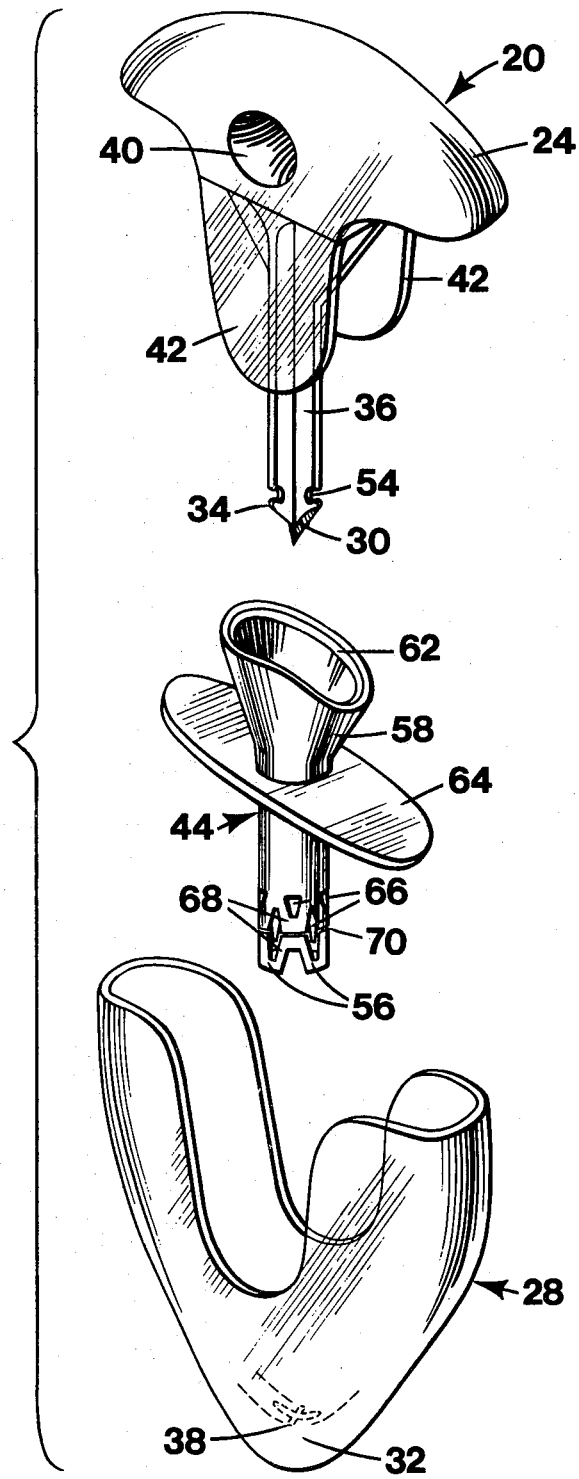
FIG. 7 is an exploded view of the inventive cricothyrotomy trocar assembly.

The lower half of the case 28, forming the scabbard, has a chamber molded inside its distal end to form a blade guard 32 and protect the carrier of the device (FIGS. 1, 7). Inclined tissue-deflecting surfaces 34 are positioned at the end of a stylet shaft 36. The tissue deflectors 34 fit into notches 38 (FIG. 7) formed inside the blade guard 32 to stabilize the distal end of the shaft 36 and to suspend the lancet tip 30 within the chamber (FIGS. 1, 7).

The stylet portion 36 of the trocar assembly 26 and the handle 24 form the upper half of the capsule (FIG. 7) which is molded as a single unit. Preferably, the shaft 36 and handle 24 are made of a plastic which is sturdy when compressed but will fatigue rapidly when twisted or flexed. A hole 40 is formed through the top of the handle 24 to enable the device to be carried on a key ring, lanyard, or the like. An embodiment of the invention specifically designed to be affixed on a utility belt would have the hole 40 formed in the lower half of the case 28, below the blade guard 32. The wearer of the utility belt could then open the capsule and ready the trocar assembly for deployment with one hand by pulling against the belt-to-scabbard attachment to separate the two halves of the capsule as described above. When separated from the scabbard 28, the opposing sides of the handle 24 form broad, thin, manipulative tabs 42 (FIG. 7) which are used to hold the device between the thumb and index finger and serve to limit the penetration of the trocar as tabs 42 come to rest against the outside surface of the throat (FIG. 10).

The stylet shaft 36 (FIG. 7) has four longitudinal fins which form four V-shaped flutes extending along its entire length. The flutes allow air to pass through a cannula 44 (FIGS. 2, 7) as the trocar 26 enters the trachea 46 (FIG. 10). The ensuing hiss of air through the cannula 44 aids in maintaining the proper position of the trocar 26 within the lumen of the trachea 46. The thin, broad, stainless steel lancet 30 is mounted transversely within the fins across the end of the shaft 36. Also formed on the end of the shaft 36, perpendicular to the lancet 30, are the two tissue-deflecting surfaces 34 which separate the tissues as the lancet 30 makes a fine incision equal in length to the outside diameter of the trocar 26 (FIGS. 2, 10). This enables the trocar 26 to pass gently through the skin and cricothyroid membrane 48 and into the trachea 46 (FIG. 10). The functional relationship of the inclined tissue deflectors 34 to the lancet 30 tends to center the trocar 26 within the cricothyroid membrane space 48 as it is inserted and precludes penetration of the thick posterior wall of the cricoid cartilage 50 and the resultant perforation of the esophagus 52.

The dimensions of the device are such that the distal end of the trocar assembly 26 comes to reset within the posterior third of the lumen of the trachea 46 when the manipulative tabs 42 of the handle 24 contact the outside surface of the throat (FIG. 10). Dovetail cutouts 54 (FIGS. 2, 7) are formed in the fins of the shaft 36 just above the lancet 30. Tabs 56 on the distal end of the cannula 44 (FIGS. 2, 7) fit into cutout 54. By design, the openings of the dovetail cutouts 54 are constricted, requiring the resilient plastic of the tabs 56 to be flexed or sprung slightly as they are pressed to place within the cutouts 54 during assembly. The snap fit of the tabs within the cutouts secures the cannula to the stylet so that the cannula can be carried through the tissues by the stylet as the trocar 26 is inserted into the trachea 46 (FIG. 10).

The cannula 44 portion of the trocar assembly 26 is preferably a single injection molded unit made of high molecular weight polyethylene, "Delrin," "Teflon," or a similar material which exhibits strength, resilience and hygenic properties. A funnel-shaped receiver 58 forms the proximal end of the cannula unit 44 and is flattened for assembly to fit between the manipulative tabs 42 of the handle 24 (FIG. 7). The taper of the funnel-shaped receiver 58 is such that a standard endotracheal tube adaptor 60 (FIG. 11) or, in another variation, the 15 mm coupling of a standard resuscitator, fits tightly and forms a seal between the adaptor 60 and the receiver 58 to prevent leakage of any ventilating gases being delivered by a resuscitator. The tight fit and seal are accomplished by the formation of an O-ring-like thickening 62 (FIGS. 7, 11) at the mouth of the receiver 58, which seals around the body of the adaptor tube 60 as the distal end of the adaptor seats against the inside wall of the receiver 58 (FIG. 11) or, in the aforementioned variation, around the outside of the funnel. If no resuscitation equipment or adaptor is available, the receiver 58 can be used as a mouthpiece (FIG. 4) for mouth-to-cannula resuscitation of an unconscious patient who is not breathing.

The stout flanges 64 projecting laterally from the body of the cannula 44 at the base of the receiver 58 protrude from between the manipulative tabs 42 of the handle 24 (FIG. 2) and are utilized to actuate the retentive distal end of the cannula 44 (FIG. 3) and to secure the cannula during and after removal of the stylet 26. The conical receiver 58, flange 64 configuration lends itself to a looping of adhesive tape which may be placed on the patient's throat across the flanges 64 and around the reciever 58 to further secure and stabilize the cannula unit 44 if resuscitation or suction equipment is used (FIGS. 11, 12).

Figure 3:
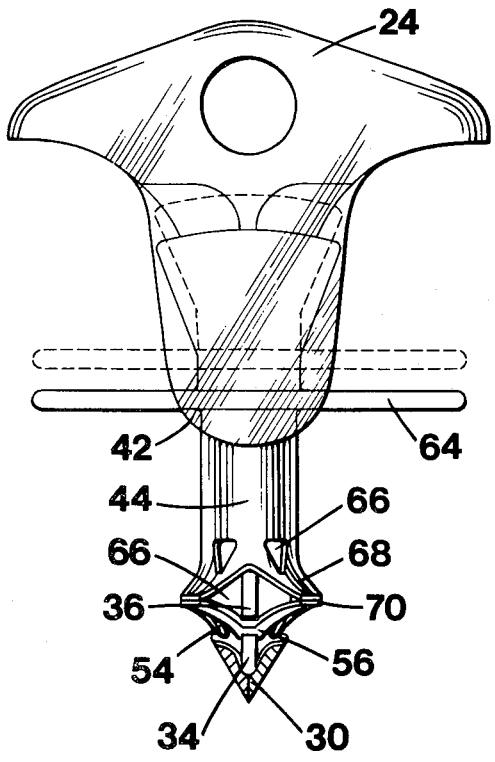
FIG. 3 is a similar elevation view of the device showing the articulation of the distal end of the cannula as the stylet is withdrawn during employment.
Figure 4:
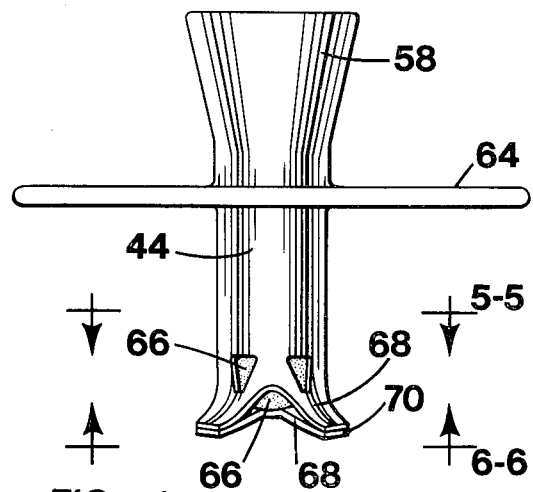
FIG. 4 is an elevation view of the cannula unit as it appears when fully deployed, showing the self-retaining flare and air passages, which passages are indicated by stippling in FIGS. 4, 5 and 6.
Figures 5, 6:
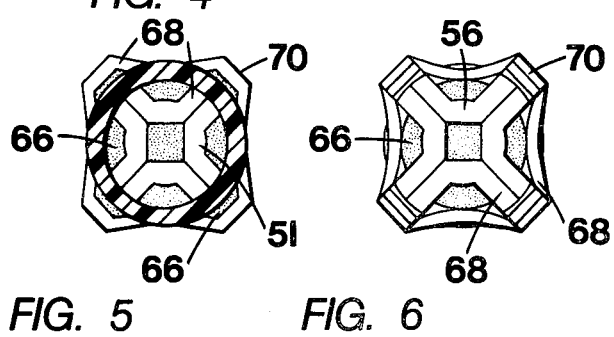
FIG. 5 is a plane view looking down from the proximal end of the cannula at a section taken along line 5—5 (FIG. 4) showing the configuration of the air passages in the flared, retentive distal end.
FIG. 6 is a plane view looking up at the flared distal end of the cannula taken along line 6—6 (FIG. 4)

The distal end of the cannula unit 44 is designed to collapse and flare outwardly as the stylet 36 is withdrawn and to retain a blossomed configuration after the stylet 36 is completely removed (FIGS. 3, 4). The self-retaining flare within the lumen of the trachea 46 prevents the cannula unit from being expelled during the patient's first forceful respirations. There are eight ports 66 in the wall of the cannula 44 at the distal end which outline the retentive intratracheal portion, provide lateral air passages, and maximize the flow of air through the cannula 44 (FIGS. 2, 3, 4, 5, 6). In FIGS. 4, 5 and 6, air passages are indicated by stippling.

The flared configuration and actuation of the intratracheal portion of the cannula 44 occur because the tabs 56 at the tip of the cannula 44 are secured within the dovetail cutouts 54 of the stylet shaft 36. These tabs 56 are attached to the cannula 44 between the ends of corresponding struts 68 which originate from the body of the cannula tube. The struts 68 outline the ports 66 and are notched to cause them to bend and form living hinges 70 in the collapsing struts. FIG. 3 shows the outline of the original position of the cannula (broken lines) and the cannula as it would appear halfway through the actuation sequence. As the body of the cannula 44 is forced down the stylet shaft 36 by depressing the flanges 64, the struts 68 flare outwardly as the tabs 56 are moved toward the center of the cannula where they brace against each other to mutually spread and hold open the end of the cannula tube. This motion completes the insertion of the cannula 44 and brings the flanges 64 of the cannula unit in contact with the surface of the throat. This does not cause further penetration of the stylet shaft 36 since the stylet is part of the stylet-handle unit 24 which includes manipulative tabs 42 which come to rest against the outside surface of the throat as the trocar is inserted.

In order to remove the stylet shaft 36 completely from the cannula 44, the flanges 64 of the cannula unit must be held securely against the throat as the stylet-handle unit 24 is withdrawn. When the retentive end of the cannula 44 is fully actuated, the collapsed struts brace against each other and the tabs on the ends of the struts snap out of the dovetail cutouts 54 in the stylet shaft as it is pulled from the cannula. After such withdrawal, the distal end of the cannula 44 retains its flared configuration (FIGS. 4, 5, 6, 11) by virtue of the resilience and memory of the plastic which causes the wider base portions of the struts 68 to act as leaf springs and stabilize themselves against each other to produce the self-retaining flare at the end of the cannula, which is now turned partially outside in. The hinge points 70 of the flared struts 68 now form the distal limit of the cannula.

If it is necessary to aspirate intratracheal mucoid secretions or blood, and if suction equipment is available, a suction catheter 72 can be passed through the cannula 44 into the trachea 46 (FIG. 12). The flared retentive end of the cannula 44 must be everted to allow the suction catheter 72 to pass through the cannula. Very little force is required to evert the flared end of the cannula and the suction catheter 72 will do this easily as it is pushed into the trachea 46 (FIG. 12).

When it becomes time to remove the cannula 44 and if aspiration procedures have not been performed, the end of the cannula 44 which is flared within the trachea 46 must be everted. The stylet portion of the trocar assembly previously withdrawn from the cannula can be blunted and used for this purpose (FIGS. 8, 9). The manipulative tabs 42 of the handle 24 are first bent out and snapped off to prevent their physical interference with the cannula's funnel-shaped receiver 58 and to enable an unrestricted insertion of the blunted stylet 36 into the cannula 44 (FIG. 9).

The blade guard chamber 32 of the scabbard 28 is used to blunt the stylet (FIGS. 7, 8). The scabbard 28 is rotated 90 degrees around its long axis and replaced over the stylet 36. The lancet 30 now comes to rest crosswise in the blade guard 32, in the notches 38 which once held the tissue deflectors 34. Pressing the lancet tip 30 into the plastic of the blade guard 32 locks the blade into the notches 38 and keys the tissue deflectors 34 into the correspondingly shaped notches. This stabilizes the shaft 36 in the scabbard 28 and prevents its rotation, thus causing the shaft 36 to fracture at its weakest point (the area of the dovetail cutouts) when the stylet-handle unit 24 and the scabbard 28 are rotated or twisted relative to each other, around the shaft axis. This leaves the sharp lancet tip 30, tissue deflectors 34, and a fragment of the stylet shaft 36 safely embedded in the scabbard 28 and produces a blunt end on the stylet shaft 36 which can now be reinserted into the cannula 44 to evert its flared distal end (FIG. 9).

After the cannula 44 is removed, the incision can be closed with surgical adhesive tape or tissue clips, leaving only a tiny hairline scar.

The procedure for application of the inventive cricothyrotomy device 20 can be modified for cases requiring greater penetration of the trocar 26 to establish entry into the lumen of the trachea 46 (patients with tumors of the neck, extremely obese individuals, etc.). Prior to insertion of the trocar assembly 26 and subsequent to the separation of the upper and lower parts of the sealed capsule, the manipulative tabs 42 of the handle are snapped off (as in the stylet blunting procedure) to enable an additional penetration of approximetly 5 mm before the flange 64 of the cannula 44 contacts the outside surface of the throat. The stylet 36 can then be withdrawn from the cannula 44 as described above.

If it is necessary to withdraw the stylet 36 from the cannula 44 without actuating the retentive intratracheal portion of the cannula, the manipulative tabs 42 of the handle 24 are snapped off prior to insertion of the trocar assembly 26 (as in the stylet blunting procedure and the procedure for obtaining additional trocar penetration). The trocar assembly 26 is inserted carefully until an airway is established and indicated by the hissing sound of air passing through the cannula 44. At this point, the stylet-handle unit 24 may be withdrawn by holding the flange 64 and receiver 58 of the cannula 44 firmly in position while rotating the stylet-handle unit approximately 45° in either direction within the cannula. This rotation will cause the release of the tabs 56 on the distal end of the cannula 44 from within the dovetail cutouts 54 on the stylet shaft 36 and enable the stylet to be withdrawn without actuating the self-retaining flare.

Those who are skilled in the art will readily perceive how to modify the system. Therefore, the appended claims are to be construed to cover all equivalent structures which fall within the true scope and spirit of the invention.

I claim:

1. An emergency cricothyrotomy trocar assembly enclosed within a functional capsular package, said assembly comprising stylet means having a short fluted shaft terminating in a lancet having at least one elongated cutting knife edge, a straight and unobstructed tube means surrounding said shaft and forming a cannula removably mounted on and deployed by said stylet cutting and penetrating the skin of a throat and a cricothyroid membranne while passing into a trachea, the flutes forming an immediate air passage during insertion while the stylet is still in the cannula, and means on said stylet and cannula for flaring the intratracheal end of the cannula to provide a self-retention means for securing the cannula within the trachea after said stylet is completely withdrawn from said cannula.

2. The assembly of claim 1 and means within parts of said capsular package for modifying the stylet for reuse during removal of the cannula from the trachea.

3. The assembly of claim 1 wherein said capsular package comprises a handle for said trocar assembly which limits the depth of penetration of the trocar into said trachea as it comes into contact with the outside surface of the throat, and scabbard means for enclosing the trocar assembly during storage, whereby the construction and design of said package during storage forms a small, durable, sealed, and presterilized container for the trocar assembly which may be carried conveniently, and means therein for attaching the package to a key ring, lanyard, or the like.

4. The assembly of claim 1 wherein the flutes on said stylet shaft are shaped and dimensioned to be long enough to penetrate the skin and cricothyroid membrane and come to rest near the posterior third to the lumen on an average adult trachea when said self-limiting handle makes contact with said throat.

5. The assembly of claim 1 wherein said stylet shaft is shaped and dimensioned to hold and carry the intratracheal end of said cannula into said trachea, and to hold the end of the cannula during actuation of said self-retaining flare.

6. The assembly of claim 1 wherein said stylet shaft terminates in said cutting edge in the form of a sharpened lancet blade means for incising the skin of the throat and the cricothyroid membrane and in tissue-deflecting surface means which guide the trocar through said skin and membrane and into the trachea.

7. The assembly of claim 1 wherein said cannula has an inside bore diameter which is larger enough to enable a patient to breathe without the aid of high-pressure ventilating equipment and to enable passage of a suction catheter for tracheal aspiration.

8. The assembly of claim 1 wherein an extratracheal portion of said cannula has a receiver means with a sealing configuration molded therein, said configuration being shaped to sealingly receive standard resuscitation equipment and said receiver being shaped for use as a mouthpiece for mouth-to-cannula resuscitation of a patient.

9. The assembly of claim 1 and a plurality of ports formed in an intratracheal portion of said cannula, said ports both providing lateral air passages and defining cannula material which forms said self-retaining flare on the cannula.

* * * * *